United States Patent [19]

Atlas et al.

[11] Patent Number: 5,298,392
[45] Date of Patent: Mar. 29, 1994

[54] PROCESS FOR DETECTION OF WATER-BORNE MICROBIAL PATHOGENS AND INDICATORS OF HUMAN FECAL CONTAMINATION IN WATER SAMPLES AND KITS THEREFOR

[75] Inventors: Ronald M. Atlas; Asim K. Bej; Meena H. Mahbubani, all of Louisville, Ky.; Richard Miller, Pekin, Ind.; Robert J. Steffan, Bismarck, N. Dak.

[73] Assignee: Hoffmann-La Roche Inc., Nutley, N.J.

[21] Appl. No.: 883,815

[22] Filed: May 13, 1992

Related U.S. Application Data

[63] Continuation of Ser. No. 467,813, Jan. 19, 1990, abandoned.

[51] Int. Cl.$^5$ ............................................. C12G 00/68
[52] U.S. Cl. ...................................... 435/600; 435/91; 436/501; 436/177; 536/23.1; 935/76; 935/78
[58] Field of Search .................... 435/6, 810, 91; 436/501, 63, 174, 177; 536/27, 23.1; 935/76, 78

[56] References Cited

U.S. PATENT DOCUMENTS

| | | | |
|---|---|---|---|
| 4,358,535 | 11/1982 | Falkow et al. | 435/5 |
| 4,683,195 | 7/1987 | Mullis et al. | 435/6 |
| 4,683,202 | 7/1987 | Mullis | 435/91 |
| 4,689,295 | 8/1987 | Taber et al. | 435/6 |

FOREIGN PATENT DOCUMENTS

WO88/03957 6/1988 PCT Int'l Appl.

OTHER PUBLICATIONS

DBA Abstract, Accession No. 89-12948; Beji et al., J. Cell. Biochem. (Suppl. 13E, 275) 1989.

Starnbach, M. N. et al., "Species-Specific Detection of Legionella pneumophila in Water by DNA Amplification and Hybridization", J. Clin. Microbiol., 27(6):1257-1261 (Jun. 1989).

Grimont, P. A. D., et al., "DNA Probe Specific for Legionella pneumophila", J. Clin. Microbiol., 21(3):431-437 (Mar. 1985).

Engleberg, N. C., et al., "DNA Sequence of mip, a Legionella pneumophila Gene Associated with Macrophage Infectivity", Infect. Immun., 57(4):1263-1270 (Apr. 1989).

MacDonell, M. T., et al., "The nucleotide sequence of the 5S rRNA from Legionella pneumophila", Nucl. Acids Res., 15(3):1335 (1987).

Cianciotto, N. P., et al., "A Legionella pneumophila Gene Encoding a Species-Specific Surface Protein Potentiates Initiation of Intracellular Infection", Infection and Immunity, 57(4):1255-1262 (Apr. 1989).

Clesceri, L. S., et al., Standard Methods for the Examination of Water and Wastewater, 17th Edition, pp. 9-14, 9-149 to 9-153 (1989).

Atlas, R. M., et al., "Detecting Bacterial Pathogens in Environmental Water Samples by Using PCR and Gene Probes", PCR Protocols: A Guide to Methods and Applications, 48:399-406 (1990).

Steffan, R. J., et al., "DNA Amplification to Enhance Detection of Genetically Engineered Bacteria in Environmental Samples", Appl. Environ. Microbiol., 54(9):2185-2191 (Sep. 1988).

Olive, D. et al., Molecular and Cellular Probes, 2, 45-57 (1988).

Clement and Hofnung, 1981, "Gene Sequence of the Lambda Receptor, an Outer Membrane Protein of E. coli K12", Cell 27:507-514.

Primary Examiner—Amelia Burgess Yarbrough
Attorney, Agent, or Firm—George M. Gould; Stacey R. Sias

[57] ABSTRACT

Processes and kits therefor for detection of water-borne pathogens and indicator organisms in water samples by recovering cells of the pathogens or indicator organisms from a water sample, lysing the cells to recover undegraded DNA, amplifying a target gene sequence of a target gene present in cells of the pathogens or indicator organisms by polymerase chain reaction amplification and detecting the presence of amplified target gene sequence to determine the presence or absence of pathogens or indicator organism in the test sample.

27 Claims, No Drawings

PROCESS FOR DETECTION OF WATER-BORNE MICROBIAL PATHOGENS AND INDICATORS OF HUMAN FECAL CONTAMINATION IN WATER SAMPLES AND KITS THEREFOR

This is a continuation of application Ser. No. 07/467,813 filed Jan. 19, 1990, now abandoned.

FIELD OF THE INVENTION

The invention relates to processes for the detection of microorganisms in samples, particularly water-borne microbial pathogens and indicator microorganisms, particularly bacteria primarily of fecal origin, in environmental samples and inclusive of aquatic and marine samples, for the purpose of preventing or source-tracing human infection, via in vitro enzymatic amplification and detection of specific genetic sequences.

BACKGROUND OF THE INVENTION

Most water-borne human pathogens cause infections and human disease via ingestion of fecal contaminated water or food. Various human parasites and pathogens are transmitted in this way, including protozoa, virus and bacteria, transmitted via human fecal contamination of water used for drinking, bathing, recreation, harvesting of shellfish, or washing/preparation of foods. Additionally, some water-borne pathogens are transmitted via contaminated aerosols and enter the human body through the respiratory tract. Legionella pneumophila, the causative agent of legionellosis fatal respiratory pneumonia infection know as Legionnaire's Disease, is transmitted in this manner. Warm stationary domestic water found in air conditioner cooling towers, inadequately chlorinated swimming pools and spas, hot water heaters, respiratory therapy equipment and shower heads, have been identified as sources of Legionella infectious outbreaks. The need for and adequacy of water purification and the safety of natural (ground and surface) waters for recreation, drinking and shellfish harvest, routinely is monitored by standard microbiological tests for fecal flora and for Legionella. The control of legionellosis requires environmental monitoring so that the reservoirs of L. pneumophila can be identified. Decontamination procedures can then be implemented in order to reduce or eliminate this bacterial pathogen, thereby reducing the risk of outbreaks of legionellosis. Additionally, the sources of L. pneumophila must be quickly determined when outbreaks of legionellosis occur to prevent additional cases.

Because many fecal pathogens are hard to assay or are infective at densities so low that water sample collection and concentration is inconvenient, fecal microbial water contamination often is assessed by testing for harder and more robust, but not necessarily pathogenic, microbes, referred to as indicator organisms, such as the "fecal coliforms", especially Escherichia coli.

The most common tests for both fecal bacteria indicator organisms and Legionella require culturing for one to several days on/or in a nutrient medium under standard conditions, followed by counting of the colonies which develop or identification of positive liquid cultures and the use of a most probably number table to determine the numbers of bacteria in the sample. Various metabolic, biochemical and immunochemical tests may be used to confirm the microbiological identities of the organisms enumerated in these tests, although they require additional time, expense and skilled labor.

Culture tests of microbiological contamination are tedious, time consuming, unsatisfactorily slow, delaying decisions which might seriously affect human health and which test should be made on the time scale of hours, not days.

There are several problems with viable culture methods used for routine monitoring of the bacteriological safety of water supplies, including the tediousness of the method, maintaining viability of bacteria between the time of collection and enumeration, lack of growth of viable but nonculturable bacteria—such as those stressed by chemicals in the water, failure to cultivate all living cells of interest, time (days) required for detection and confirmation of enteric bacteria, lack of specificity for detection of true fecal coliforms such as E. Coli, failure to distinguish living from dead cells using direct microscopic counts, and misidentification of organisms due to antigenic cross reactivity using serological procedures.

Usually such culture tests are not as specific or as sensitive as desirable to ensure with sufficient certainty the presence or absence of specific microbes in low numbers. Gene probes that specifically hybridize with the DNA of specific regions associated with specific pathogens or indicator organisms provides a means of specific detection but conventional gene probe methods are generally about 10,000 times less sensitive than required for environmental monitoring purposes.

Recently, tests based upon detection of $\beta$-D-glucuronidase, such as the Colilert test, have been suggested as alternate approaches for detecting coliforms. Enzymatic transformation of the fluorogenic substrate 4-methylunbelliferyl-$\beta$-glucuronidide or colorimetric substrate p-nitrophenyl glucuronide is indicative of the presence of E. coli, but detection of such enzymatic activity still requires culturing of bacteria. It has also recently been reported that basing a test on $\beta$-D-glucuronidase activity may fail to detect a significant proportion, about 30%, of fecal coliform bacteria in some cases because of occurrences of high incidences of $\beta$-D-glucuronidase negative E. coli.

The traditional methods for the detection of L. pneumophila are the viable plate count and the direct microscopic count, the latter by using several commercially available fluorescent antibody reagents. Although cultivation of viable cells of Legionella from water samples is a standard procedure, it is tedious and time consuming. Additionally, cultivation methods may underestimate numbers of viable cells because some cells of L. pneumophila are sensitive to the acid-wash treatment and selective media used in the standard viable enumeration procedure. Also, some cells may be viable but nonculturable. The serological detection of Legionella using polyclonal antibody reagents likewise has limitations because immunofluorescence microscopy cannot distinguish living from dead cells and also some non-Legionella cells show false positive reactions due to antigenic-cross reactivity.

Detection of Legionella has been reported by colony hybridization using a radiolabelled unique DNA gene probe fragment isolated from Legionella chromosomal DNA after restriction enzyme digestion. In waters with high microbial populations, as are found in water cooling towers, the level of detection sensitivity by colony hybridization would be about $10^4$/ml. A sensitivity of $5 \times 10^4$ cells was achieved by using a separate gene probe. A commercial gene probe detection kit, based upon rRNA detection, has a sensitivity of $10^3$ or $10^4$ cells.

It is therefore highly desirable that a process and kits therefor be available for detection of water-borne microbial pathogens and indicators of human fecal contamination in natural environmental, purified or other water sources in which the aforementioned problems are eliminated or substantially reduced. A further object of the invention is to provide such a process and kits which have greater specificity and sensitivity to ensure detection of the pathogens or indicators at very low concentrations. A still further object of this invention is to provide such a process and kits therefor which enable the noncultural detection of such pathogens and indicators. Another object of this invention is to provide such process and kits therefor which detect nonculturable coliforms. It is also an object of this invention to provide such a process and kits therefor which enable the detection of such pathogens and indicators in a matter of hours rather than days. It is a still further object of this invention to provide a process and kits therefor which permit direct detection of pathogens in water samples, rather than relying upon the indirect detection of indicator organisms.

An additional object of this invention is to provide an effective, specific and sensitive process and kits therefor for detection of sources of Legionella so as to prevent or determine the sources of outbreaks of legionellosis. A still further additional object of this invention is to provide such a process and kits therefor for specific detection of *L. pneumophila* for both clinical diagnosis and environmental monitoring or source tracing of *L. pneumophila*. It is another object of this invention to provide such a process an kits therefor in which one can detect both all Legionella species and all *L. pneumophila* serotypes in the same water sample at the same time.

An additional object of this invention is to provide a process and kits therefor which will detect substantially all species and strains which fall in the microbial pathogens or indicator class and no organisms from other species or genera. A still further object is to provide such a process and kits therefor which employ a highly polymorphic sequence within the target gene to permit distinction among variants and in some other cases to avoid any distinction among variants of the same target species, genus or other defined group.

SUMMARY OF THE INVENTION

Detection of water-borne pathogens and indicator organisms, particularly bacteria primarily of fecal origin, in water samples is accomplished according to this invention by a process, and kits therefor, wherein:

1) a water test sample is treated in such a way that substantially all the water-borne pathogens and indicator microorganisms (the targeted cells) are recovered and concentrated, preferably into a volume on the order of about 0.1 to 1 ml.

2) the concentrated test sample is treated to lyse cells and recover substantially undegraded targeted DNA, essentially free of potentially interfering chemicals or biochemicals, especially proteins, in a small fraction of about 1 ml of water or aqueous buffer.

3) a target gene and target DNA nucleotide sequence from that gene is chosen and the target DNA nucleotide sequence of the test sample is incubated under amplification conditions wherein selected primers hybridize to separated (denatured) target strands of the target DNA sequence and polymerase extends the primers to make fully double-stranded replicas of the target DNA sequence, and 4) amplified target DNA sequence is detected, and optionally quantified, to determine the presence or absence in the test sample of pathogen or indicator organism carrying the selected target DNA sequence.

DETAILED DESCRIPTION OF THE INVENTION

According to the present invention, specific DNA target gene sequences are selected and amplified in vitro such that the targets DNA sequences can be detected even when they are present in very low concentrations in test samples, particularly in very low concentrations relative to high non-target backgrounds. In the present invention, a target nucleotide sequence is selected for amplification and is amplified in a manner such that the concentration of target nucleotide sequence can increase as much as two-fold for each amplification or cycle or as much as 1024-fold for each series of ten amplification cycles.

This invention provides a process for detecting water-borne microorganisms, pathogens and bacteria which serve as indicator of the probable presence of pathogens, primarily of fecal origin, in which said method comprises recovering said microorganisms from water, often from large volumes of water, lysing the microorganisms to release substantially undegraded DNA from the pathogens or indicator organisms, selecting a target gene and target nucleotide sequence from that target gene and amplifying the specific target DNA sequence with a primer pair that hybridizes to separated target strands of the target DNA sequence and with polymerase to extend the primers to make fully double-stranded replicas of the target DNA sequence, detecting amplified target DNA sequence and concluding from the success or failure to detect amplified target DNA sequence whether or not the original test sample contained the microorganism carrying the target DNA sequence.

The specific target genes for particular water-borne human pathogens and indicators of human fecal contamination useful in the process of this invention include the following: lacZ for Escherichia, Enterobacter, Citrobacter and Klebsiella species; lamB for Escherichia, Salmonella, and Shigella species; 5S ribosomal RNA for Legionella species; mip for *Legionella pneumophila;* UidA for *Escherichia coli, Shigella sonnei* and *Shigella flexineri;* and UidC for *Escherichia coli* and *Shigella sonnei.*

Specific DNA nucleotide sequences from each of these target genes are selected for amplification by use of primer pairs for each selected gene sequence, which primers comprise selected sequences from each of the selected gene sequences and are exemplified hereinafter.

Amplification of the target DNA sequence is by means of selected primer pairs according to a procedure known as Polymerase Chain Reaction, hereinafter referred to simply as PCR. PCR amplification of nucleotide sequences is described in U.S. Pat. No. 4,683,202 of K. Mullis, issued Jul. 27, 1989 and assigned to Cetus Corporation, the disclosure of which is incorporated herein by reference thereto. As described in said patent, the PCR amplification process comprises amplifying a selected or targeted nucleic acid sequence on the order of about 100–1000 bp in length by treating the two separate complementary strands of the nucleic acid sequence with two oligonucleotide primers, each being complementary to one of the two strands, to anneal the primers to their complementary strands, then synthesizing extension products of said primers by polymerase to extend said primers to make fully double-stranded replicas of the selected target nucleic acid sequence, followed by separation (denaturation) of the extension products and repeating this amplification sequence the desired number of cycles to increase the concentration of the selected nucleic acid sequence.

In the PCR amplification step of the process of the present invention, the reaction mixture is repeatedly cycled between (1) a low temperature, generally of from about 37° to 70° C., for primer annealing to the selected target sequence or for strand reassociation, (2) an intermediate temperature, generally of from about 70° to 80° C., for polymerase extension of the primers, and (3) a higher temperature, generally of from about 80° to 100° C., for denaturation of separation of the strands. Although three temperature ranges have been described, it is often possible that the amplification process can be adequately conducted between two of the temperature ranges. Each thermal cycle of the two or three temperatures can increase the concentration of the amplified target DNA sequence as much as two-fold, so that every series of ten amplification cycles can increase the concentration as much as 1024-fold. If a thermostable DNA polymerase, such as that purified from the bacterium *Thermus aquaticus* (Taq) is used, the polymerase reaction can be cycled many times, typically 20-40 times, between the two or three temperatures without need to augment the initially added polymerase enzyme.

Specific DNA sequences from each of the target genes sequences may be selected to serve as hybridization probes for detection of successful target DNA sequence amplification by direct and reverse gene probe hybridization. Detection of successful target DNA sequence amplification may also be accomplished by any suitable DNA molecule detection method, such as for example, those methods which separate DNA molecules primarily on the basis of size such as gel electrophoresis, anion-exchange HPLC and paired-ion reverse-phase HPLC.

The various aspects of the process and kits of this invention are described in more detail hereinafter. The initial aspect of the process comprises recovery, into a small test sample volume of water on the order of about 0.1 to about 1.0 ml, of substantially all the cells of the targeted water-borne pathogens or indicator organisms from a water sample which can comprise a sample many orders of magnitude larger than the small volume of the test sample in which the amplification step takes place, i.e. from a volume of water potentially as large as several liters and which may contain non-targeted background cells in a concentration many orders of magnitude larger than the targeted cells. Next, essentially all target cells are treated in such a manner, such as by lysis, that essentially all undegraded target DNA sequences are recovered from the target cells so as to be sufficiently free of potentially interfering substances, such as enzymes, low molecular weight inhibitors or other components that might interfere with enzymatic amplification of the target DNA sequences. A target DNA sequence from the target gene and a pair or primer sequences and PCR reaction conditions are selected for performing PCR amplification of the target DNA sequence in such a manner that efficient and specific amplification of the segment of targeted DNA sequence between the location of the two primers on the targeted sequence of essentially all organisms within the targeted taxonomic subset and none from outside the targeted group occurs. Following PCR amplification of targeted DNA sequences, amplified targeted DNA is detected by sufficiently sensitive and specific detection methods. Although isotopic detection means may be employed, it is preferred, for reasons of safety and convenience, that a suitable nonisotopic detection means be employed. Preferably detection is by means of suitable hybridization probes utilizing probes of specific DNA sequences from each of the targeted genes sequences. Quantification of the amplified target DNA sequences may also be carried out, if desired.

The operation of recovering substantially all the targeted cells from a water sample may be performed by any of several suitable means, including, for example, filtration and centrifugation, possibly with the help of suspended or dissolved additives which serve to capture or flocculate the target organisms in a physical state which facilitates their separation. If the microorganisms are not adsorbed to much larger particles or flocculated, the nominal filter pore size should be no larger than about 0.2 to 0.5 μm, preferably about 0.45 μm, to assure efficient capture. If the microorganisms are recovered in a gel or adsorbed to particles, much larger filter pore sizes are preferred to accelerate filtration. Preferred cell recovery according to this invention is obtained by centrifugation from small volume samples, about 1 mL or less, and by filtration for small or large, typically 100 mL, volume samples. Especially preferred cell recovery by filtration of this invention is by passage through 11-13 mm diameter 0.20-0.50 μm pore size polycarbonate or Teflon filters.

The operation of treating the recovered cells in the test sample in such a manner that essentially all undegraded target DNA sequences are recovered from the target cells may be performed by any of many suitable methods. Recovery of the target DNA sequences by microbial lysis may be effected by brief exposure to extremes of pH, organic solvents, chaotropic agents like urea and quanidine HCl, detergents like sodium dodecyl sulfate (SDS) and Triton X-100, osmotic shock, lysozyme digestion, or protease digestion and the like. Interfering substances can be removed, for example, by organic solvent extraction, acid precipitation, ultrafiltration, solid-phase extraction, HPLC, LiCl precipitation, protease digestion, RNase digestion, or polyethylene glycol precipitation and the like. Solid-phase extraction or HPLC can be based on ion-exchange, reverse-phase, hydrophobic-interaction, or silica-gel adsorption interactions. Preferred release of DNA from target cells of this invention is by use of a SDS-lysozyme treatment and specifically for Legionella by the alternation of freeze (−70° C.) thaw (25° C.) cycles.

A wide variety of genes and an even wider range of gene subsequences can be selected in order to perform the PCR amplification step of the process of this invention. Once the range of the target genera, species, strains and serotypes has been specified on the basis of knowledge about pathogenicity or occurrence in human feces (but not in the pristine natural environment except as a result of fecal contamination), one selects a gene and target subsequence present in the target organisms and absent in essentially all others. Often subsequences within a gene differ widely in polymorphism, a fact that can be used to advantage in environmental microbial monitoring. Primers for the PCR amplification steps of the process of this invention may be chosen which efficiently amplify all organisms within a larger target set by locating them in non-polymorphic subsequences separated by approximately 100–1000 bp, and oligonucleotide probes are constructed to be complementary to about 10–30 nucleotide sequences on complementary strands of the targeted DNA sequence and hybridize efficiently to sequences within the amplified region to ensure specificity to the target organism species, genus or group.

As examples of specific target genes for carrying out the present invention there may be mentioned, for example, the following: lacZ to detect total coliform bacteria that are useful indicators of human fecal contamination, including Escherichia species, Enterobacter species, Citrobacter species and Klebsiella species; lamB to detect the coliform bacterial species Escherichia coli which is a useful indicator of human fecal contamination, and the enteric pathogenic bacteria in the genera Salmonella and Shigella, which cause human disease and which are found in association with human fecal contamination; the 5S ribosomal RNA gene to detect all Legionella species, mip to detect the pathogen Legionella pneumophila, UidA to detect the coliform bacterial species Escherichia coli and the enteric pathogens Shigella sonnei and Shigella flexineri; and UidC to detect the fecal coliform indicator bacterium species Escherichia coli and the enteric pathogen Shigella sonnei.

The nucleotide sequences of these genes are previously known, which facilitates their selection and use as targets for PCR DNA amplification, but the abilities of PCR amplifications of these specific genes to provide a basis for detecting the defined target groups was not known nor was it apparent that they would provide a basis for doing so prior to this invention. Our invention includes the following new and novel discoveries: (1) the lacZ gene contains a sufficiently conserved region to permit PCR amplification and gene probe detection not only of E. coli (the bacterial species for which the sequence of the gene had previously been determined), but as well as the other Gram negative lactose utilizing bacteria that constitute the group of enteric bacteria (which were not known to have this sequence), and that this conserved region does not occur in non-enteric Gram negative bacteria nor in the Gram positive-lactose utilizing bacteria—hence, lacZ is a suitable target for detection of "total" coliform bacteria; (2) the lamB gene contains a sufficiently conserved region to permit PCR amplification and gene probe detection not only of E. coli (the bacterial species for which the sequence of the gene had previously been determined), but as well as for Salmonella and Shigella species (which were not known to have this sequence), and that this conserved region does not occur in other Gram negative or Gram positive bacteria—hence, lamB is a suitable target for detection of the fecal indicator coliform bacterial species E. coli and the enteric pathogens of greatest concern in fecal contaminated environments—namely Salmonella and Shigella; (3) the DNA encoding a 5S rRNA sequence contains a sufficiently conserved region to permit PCR amplification and gene probe detection of all Legionella species and that this conserved region does not occur in other bacterial species—hence a region of DNA encoding 5S rRNA is a suitable target for detection of all Legionella species; (4) the mip gene of L. pneumophila contains a sufficiently conserved region to permit PCR amplification and gene probe detection of all serotypes of L. pneumophila and that this conserved region does not occur in other Legionella species or other bacteria—hence, mip is a suitable target for detection of L. pneumophila; and (5) the UidA gene sequence, and also the UidC sequence (the controller region of the UidA gene) both contain a region which permits PCR amplification and gene probe detection of E. coli and some Shigella species, and this region does not occur in other Gram negative or Gram positive bacteria—hence, UidA and UidC are suitable targets for detection of the fecal indicator coliform bacterial species E. coli and some Shigella species.

Specifically preferred gene subsequences for use in the process of this invention are defined by the following primer pairs:

5'-GGTTTATGCAGCAACGAGACGTCA or
5'-CACCATGCCGTGGGTTTCAATATT and
5'-ATGAAAGCTGGCTACAGGAAGGCC for lacZ;
5'-CTGATCGAATGGCTGCCAGGCTCC and
5'-CAACCAGACGATAGTTATCACGCA and also the pair
5'-GGATATTTCTGGTCCTGGTGCCGG and
5'-ACTTGGTGCCGTTGTCGTTATCCC for lamB;
5'-GCTACAGACAAGGATAAGTTG and 5'-GTTTTGTATGACTTTAATTCA for mip;
5'-AGAACCGCTGATATCGCTAAAC and 5'-TAGGACCGCTACTGGATGAA,
5'-GCGATGACCTACTTTCGCAT for 5S rRNA;
5'-AAAACGGCAAGAAAAAGCAG and 5'-ACGCGTGGTTACAGTCTTGCG, and also 5'-TATGGAATTTCGCCGATTTT and
5'-TGTTTGCCTCCCTGCTGCGG and also the pair
5'-AAAACGGCAAGAAAAAGCAG and 5'-TGTTTGCCTCCCTGCTGCGG for UidA; and
5'-TGTTACGTCCTGTAGAAAGCCC and 5'-AAAACTGCCTGGCACAGCAATT for UidC.

Effective primers may also be constructed not only from these subsequences, but from sequences which are contained within them, sequences which overlap them substantially, that is, by approximately 10 bp, sequences within the target gene, and sequences that encompass the target gene.

After recovery of substantially undegraded target DNA in a small volume of about 1 ml of water or aqueous buffer and selection of the appropriate oligonucleotide primer pair for the targeted DNA sequence, complementary to about 10–30 nucleotide sequences on complementary strands of the targeted DNA sequence, the target DNA is incubated with dNTP's, $Mg^{+2}$, a DNA polymerase and the oligonucleotide primers under conditions where the primers hybridize to the separated (denatured) target DNA strands and the polymerase extends the primers to make fully double-stranded replicas of the target sequence. Choice of PCR amplification conditions, such as temperatures, incubation times, solvents, enzyme choice, reagent concentrations, equipment and the like, are chosen to give efficient and specific amplification of the target DNA sequence. It will be readily understood that the effective and optional conditions for each process step and parameter will differ significantly among the various target organisms, the various kinds of test samples, target DNA sequence and primer pairs selected. Solvent choice, enzyme choice and concentration, primer concentration, dNTP concentration, and equipment choice for performing thermal cycles with sufficiently well controlled temperatures and incubation times are generally understood by those skilled in the art of PCR amplification of DNA. Choice of exact temperatures and incubation times for the specific target sequences of the invention may be determined by trial and error, monitoring the quantity and quality of amplified DNA such as by agarose or polyacrylamide gel electrophoresis after staining of DNA with a fluorescent dye such as ethidium bromide. One selects reaction conditions which maximize the yield of an electrophoretic band of target DNA with the size expected to be defined by the chosen primers and minimize, or preferably completely prevent, amplification of any other DNA.

As examples of specifically preferred conditions for conducting PCR DNA amplification of this invention, there may be mentioned: initial denaturation at 94° C. for 2 min, reannealing temperature of 50° C. for 30 sec, extension temperature of 72° C. for 60 sec, denaturation temperature of 94° C. for 60 sec, magnesium concentration 1.5 mM, and native tag polymerase for lacZ; initial denaturation of 94° C. for 2 min, reannealing temperature of 60° C. for 30 sec, extension temperature of 72° C. for 30 sec, denaturation temperature of 94° C. for 60 sec, magnesium concentration 1.5 mM, and native tag polymerase for lamB; initial denaturation at 94° C. for 3 min, reannealing temperature of 50° C. for 60 sec, extension temperature of 72° C. for 60 sec, denaturation temperature of 94° C. for 60 sec, magnesium concentration 1.5 mM, and either native tag polymerase or amplitag for Legionella DNA encoding 5S rRNA; initial denaturation at 94° C. for 3 min, reannealing temperature of 50° C. for 60 sec, extension temperature of 72° C. for 60 sec, melting temperature of 94° C. for 60 sec, magnesium concentration 1.5 mM, and either native tag polymerase or amplitag for mip; and initial denaturation at 94° C. for 3 min, reannealing and extension at 50° C. for 1 min, denaturation at 94° C. for 60 sec, magnesium concentration 1.5 mM and native tag polymerase for UidA and UidC.

Amplified target DNA can be detected by any suitable variety of means. Separation of the amplified PCR target DNA product, sideproducts, and unreacted reagents by HPLC can provide a rapid quantitative report on the presence or absence of amplified DNA of the expected size range. HPLC columns may, for example, be based on ion exchange, paired-ion reverse-phase, or size exclusion separations. The column effluent is generally most simply detected and quantitated by ultraviolet absorbence in the 250–280 nm spectral region, although fluorescent monitoring, after post-column derivatization with a fluorescent DNA-binding dye, and electrochemical detection also are possible and generally are potentially more sensitive than spectrophotometry. Separation of amplified PCR target DNA product, sideproducts, and unreacted reagents by gel electrophoresis, followed by DNA staining with a fluorescent or absorbing dye, also reports on the presence or absence of amplified DNA in the expected size range. However, these analytical signals are harder to quantitate.

A preferred mode of detecting PCR amplified DNA target sequence is via hybridization to a single-stranded oligonucleotide probe which is sequence-complementary to a DNA subsequence located between the two selected oligonucleotide primers in the target gene. If the PCR amplified target DNA sequence is denatured and captured on a solid support, such as a nylon or nitrocellulose membrane, the probe may be radioactively tagged or attached directly or indirectly to an enzyme molecule. Then, after incubation of membrane-captured PCR amplified target DNA sequence product with the probe under hybridization conditions, excess probe can be washed away and detection can be by autoradiography or radiation counting, radioactive probe, or by exposure to a chromogenic or fluorogenic substrate of the probe-attached enzyme. If the oligonucleotide hybridization probe has been attached to a solid support, the incubation of denatured PCR amplified target DNA sequence product with the solid support under hybridizing conditions results in immmobilization of said PCR product. If the PCR product contains biotin or some other chemical group for which there are specific binding molecules, like avidin and antibodies, then the immobilized product can be detected with an enzyme attached to the specific binding molecule, such as horseradish peroxidase or alkaline phosphatase attached to streptavidin.

Preferred means of detection of PCR amplified target DNA sequence product of this invention are by using hybridization with radioisotopically labelled gene probes and biotinylated gene probes. Especially preferred detection of PCR amplified target DNA sequence product of this invention is by using reverse-blotting hybridization in which the amplified DNA is labelled during PCR amplification by incorporation of biotin from biotinylated dUTP or biotinylated primers and by use of poly-T-tailed gene probes affixed to membranes.

Preferred gene probe sequences for detection of target DNA gene sequences of this invention include the following:
5'-TGACGTCTCGTTGCTGCATAAACCGAC-TACACAAATCAGCGATTTCCATT or the complement of this sequence for lacZ;
5'-TGCGTGATAACTATCGTCTGGTT-GATGGCGCATCGAAAGACGGCTGGTTG or the complement of this sequence for lamB;
5'-TTTGGGGAAGAATTTTAAAAATCAAGG-CATAGATGTTAATCCGGAAGCAA or the complement of this sequence for mip;
5'-CTCGAACTCAGAAGT-GAAACATTTCCGCGCCAATGATAGT or the complement of this sequence and
5'-BCTCGAACTCAGAAGT-CAAACATTTCCGCGCCAATGATAGTGT-GAGGCTTC wherein B is biotin or the complement of this sequence for Legionella 5S rRNA;
5'-TGCCGGGATCCATCGCAGCGTAATGCT-CTACACCACGCCGAACACCTGGG or the complement of this sequence and
5'-AAAGGGATCTTCACTCGCGACC-GCAAACCGAAGTCGGCGGCTTTTCTGCT or the complement of this sequence for UidA; and
5'-CAACCCGTGAAATCAAAAAACT-CGACGGCCTGTGGGCATT or the complement of this sequence for UidC.

A further aspect of this invention comprises kits suitable for use in carrying out the PCR amplification and detection process of this invention. Such test kits, designed to facilitate the amplification and detection of a water-borne pathogen or indicator organism, will generally comprise a primer pair consisting of two oligonucleotide primers complementary to about 10–30 nucleotide sequences on complementary strands of a targeted DNA sequence in a target gene of said pathogen or indicator organism, and a probe sequence for detection of said targeted DNA sequence and optionally a control DNA template of said targeted DNA sequence. The test kits may comprise published instructions and reagents for the PCR amplification and detection of the targeted DNA sequence. In addition to the aforementioned primer pairs and probe sequence, the test kit may also include other reagents for the PCR amplification of the targeted DNA sequence, such as for example, lysing agents, PCR amplification polymerase and the like, and filtration devices for water sample collection.

Preferred test kits according to this invention comprise the aforementioned preferred primer pairs and the corresponding preferred probe sequences also mentioned hereinbefore, and optionally a control ENA template of the targeted DNA sequence. For example, a test kit for detection of Escherichia, Enterobacter, Citrobacter, and Klebsiella species may comprise the primer pairs 5'-GGTTTATGCAGCAAC-GAGACGTCA or 5'-CACCATGCCGTGGGTTT-CAATATT and 5'-ATGAAAGCTGGCTACAAG-GAAGGCC and the gene probe 5'-TGACGTCTCGTTGCTGCATAAACCGAC-TACACAAATCAGCGATTTCCATT or the complement of this sequence for amplification of a sequence in the LacZ gene and for detection of an amplified sequence in said lacZ gene. A test kit for detection of Escherichia coli, Salmonella and Shigella species may comprise the primer pairs 5'-CTGATC-GAATGGCTGCCAGGCTCC and 5'-CAAC-CAGACGATAGTTATCACGCA or 5'-GGATATTTCTGGTCCTGGTGCCGG and 5'-ACTTGGTGCCGTTGTCGTTATCCC and the gene probe 5'-TGCGTGATAACTATCGTCTGGTT-GATGGCGCATCGAAAGACGGCTGGTTG or the complement of this sequence for amplification of a sequence in the lamB gene and for detection of an amplified sequence in said lamB gene. A test kit for detection of Legionella species may comprise the primer pairs 5'-AGAACCGCTGATATCGCTAAAC and 5'-TAGGACCGCTACTGGATGAA and the gene probe 5'-CTCGAACTCAGAAGT-GAAACATTTCCGCGCCAATGATAGT or the complement of this sequence for amplification of a sequence in the Legionella 5S ribosomal RNA gene and for detection of an amplified sequence in said Legionella 5S ribosomal RNA gene. A test kit for detection of Legionella species may also comprise the primer pairs 5'-ACTATAGCGATTTGGAACCA and 5'-GCGATGACCTACTTTCGCAT and the biotinylated gene probe 5'-BCTCGAACTCAGAAGT-CAAACATTTCCGCGCCAATGATAGTGT-GAGGCTTC or the complement of this sequence for amplification of a sequence in the Legionella 5S ribosomal RNA gene and for detection of an amplified sequence in said Legionella 5S ribosomal RNA gene. A test kit for detection of Legionella pneumophila may comprise the primer pairs 5'-GCTACAGACAAG-GATAAGTTG and 5'-GTTTTGTATGACTT-TAATTCA and the gene probe 5'-TTTGGGGAAGAATTTTAAAAATCAAGG-CATAGATGTTAATCCGGAAGCAA or the complement of this sequence for amplification of a sequence in the mip gene and for detection of an amplified sequence in said mip gene. A test kit for detection of Escherichia coli, Shigella sonnei and Shigella flexineri may comprise the primer pairs 5'-AAAACG-GCAAGAAAAAGCAG and 5'-ACGCGTGGTTACAGTCTTGCG, and the gene probe 5'-TGCCGGGATCCATCGCAGC-GTAATGCTCTACACCACGC-CGAACACCTGGG or the complement of this sequence or the primer pairs 5'-TATGGAATTTCGC-CGATTTT and 5'-TGTTTGCCTCCCTGCTGCGG and the gene probe 5'-AAAGGGATCTTCACTCG-CGACCGCAAACC-GAAGTCGGCGGCTTTTCTGCT or the complement of this sequence or the primer pairs 5'-AAAACG-GCAAGAAAAAGCAG and 5'-TGTTTGCCTCCCTGCTGCGG and either of the gene probes 5'-TGCCGGGATCCATCGCAGC-GTAATGCTCTACACCACGC-CGAACACCTGGG or 5'-AAAGGGATCTT-CACTCGCGACCGCAAACC-GAAGTCGGCGGCTTTTCTGCT for amplification of a sequence in the UidA gene and for detection of an amplified sequence in said UidA gene. A test kit for detection of Escherichia coli and Shigella sonnei may comprise the primer pairs 5'-TGTTACGTCCT-GTAGAAAGCCC and 5'-AAAACTGCCTG-GCACAGCAATT and the gene probe 5'-CAACCCGTGAAATCAAAAAACT-CGACGGCCTGTGGGCATT or the complement of this sequence for amplification of a sequence in the UidC gene and for detection of an amplified sequence in said UidC gene. It will be understood that each of these exemplified test kits may also contain other components or reagents, such as a filtration device for water sample collection, PCR amplification polymerase, such as native tag polymerase or amplitag polymerase and a control DNA template for the target gene sequence.

The invention is illustrated by the following exemplary tests, and the results thereof, for the recovery, PCR amplification and detection of water-borne coliform and Legionella bacteria.

FECAL COLIFORM AND ENTERIC PATHOGENS

Recovery of Coliform DNA

Two methods were used to recover DNA from bacterial cells. In one method, total genomic DNA was extracted from cultures by a procedure in which target DNA from bacterial cells in 1.5 ml samples of overnight cultures were released by alkaline lysis with sodium dodecyl sulfate (SDS) treatment. Proteinase K (Sigma, St. Louis) and CTA8:NaCl were used to remove proteins and carbohydrates and the DNA was further purified by using chloroform:isoamyl alcohol (24:1) and phenol:chloroform:isoamyl alcohol (24:24:2) extractions followed by precipitation with isopropanol. After centrifugation at 12,000×g for 15 min, the pelleted DNA was washed once with cold 70% alcohol and dried under vacuum. Using this procedure about 100–150 μg of purified genomic DNA was recovered from each sample.

In a simpler direct lysis method of recovery of target DNA from bacterial cells, cells were recovered from a 100 ml water sample, to which bacterial cells had been added. Cells were collected by centrifugation at 10,000×g for 15 min. The cells were transferred to 0.6 ml Eppendorf tubes and after centrifugation for 5 min at 12,000×g, the cell pellets were resuspended in 20 μl lysis solution containing 1×PCR buffer, 0.05 mg per ml proteinase K, 20 mM dithiothreitol (DTT) and 1.8 μM SDS; the samples were vortexed for 15 sec and incubated at 37° C. for 1–1.5 h, after which they were heated to 85°–90° C. for 5 min to inactivate the proteinase K.

Then an additional 10 μl of PCR buffer, dNTPs, Taq polymerase and primers were added and PCR amplification was performed as described.

PCR Amplification and Targeted DNA Coliform Sequences

PCR amplification was performed using a DNA Thermal Cycler and native Taq polymerase (Perkin Elmer Cetus Corp.). The PCR solution used contained 1×PCR amplification buffer (10×buffer contains 50 mM KCl, 100 mM Tris-Cl, pH 8.13, 15 mM MgCl$_2$ and 0.1% (w/v) gelatin), 200 μM each of the dNTPs, 0.2-1 μM of each of the primers, 1 ag ($10^{-18}$ g)—1 μg template DNA, 2.5 units Taq DNA polymerase, and double distilled water containing 0.1% diethylpyrocarbonate (DEPC). Template target DNAs were initially denatured at 94° C. for 1-3 min. Then a total of 25-40 PCR cycles were run using the following conditions: denaturation at 94° C. for 0.5-1 min, primer annealing at 40°, 50°, 60° or 70° C. for 0.5-1 min, DNA extension at 72° C. for 1-2 min. Oligonucleotide primers were synthesized using a Systec DNA synthesizer and purified using an oligonucleotide Purification Cartridge (Applied Biosystems, Foster City, Calif.) for small samples and reverse-phase HPLC with a C-8 3 micron reverse-phase column (Perkin Elmer) for large samples.

An 876 bp region of E. coli lacZ gene, based upon the sequence reported by Kalnins et al., EMBO J. 2:593–597 (1983), was amplified by using 24 mer primers ZL-1675, 5'-ATGAAAGCTGGCTACAG-GAAGGCC, and ZR-2548, 5'-CACCATGCCGTGGGTTTCAATATT. Primer ZL-1675 was located between 1675 bp and 1698 bp and primer ZR-2548 was located between 2525 bp and 2548 bp within the coding sequence of lacZ gene of E. coli. A second 24 mer primer ZR-2025, 5'-GGTTTATGCAG-CAACGAGACGTCA, was used along with primer ZL-1675 to amplify a shorter 326 bp region of lacZ. Primer ZR-2025 was located between 2001 bp and 2025 bp which is a region nearer the amino terminal of the E. coli lacZ gene than the primer sequence ZR-2548.

A 554 bp sequence downstream from the sequence encoding the lambda attachment site peptide of lamB, based upon the sequence reported by Bedouelle et al., Nature 285:78-81 (1980), was amplified by using two 24 mer primers. Primer BL-4899, 5'-GGATATTTCTGGTCCTGGTGCCGG, was located between 4899 bp and 4922 bp and primer BR-5452, 5'-ACTTGGTGCCGTTGTCGTTATCCC, was located between 5429 bp and 5452 bp. A second set of 24 mer primers were also used to amplify a 309 bp segment of the coding region of the lamB gene of E. coli. These primers were designated BL-4910, 5'-CTGATCGAATGGCTGCCAGGCTCC, which was located between 4910 bp and 4933 bp, and BR-5219, 5'-CAACCAGACGATAGTTATCACGCA, which was located between 5195 bp and 5219 bp.

In some examples, regions of lacZ and lamB were amplified simultaneously by using mixtures of primers ZL-1675 and ZR-2548 for lacZ and BL-4899 and BR-5452 for lamB. In these examples 50 ng-1 μg target genomic DNAs and varying relative concentrations of primers (0.125-1.0 μM of each primer) were used.

The position numbers for lamB and lamZ sequences are based on those assigned in the NIH-BIONET data bank.

Fecal coliform and enteric pathogens are also successfully amplified and detected according to this invention in a similar manner when a 147 bp region of the E. coli UidA gene, based on the sequence reported by Jefferson et al., PNAS, 83:8447–8451 (1986), was amplified by using the primers 754L-1, 5'-AAAACG-GCAAGAAAAAGCAG, and 879R-1, 5'-ACGCGTGGTTACAGTCTTGCG, which are located between 754 bp and 773 bp and 880 and 900 bp, respectively, and using the gene probe UidA-1, 5'-TGCCGGGATCCATCGCAGCGTAATGCT-CTACACCACGCCGAACAGGTGGG, which is located between 800 bp and 849 bp, for detection of the amplified UidA gene; a 166 bp region of the UidA gene was amplified by using the primers 1939L-1, 5'-TATG-GAATTTCGCCGATTTT, and 2085R-1, 5'-TGTTTGCCTCCCTGCTGCGG, which are located between 1939 bp and 1958 bp and 2085 bp and 2104 bp, respectively, and using the gene probe UidA-2, 5'-AAAGGGATCTTCACTCGCGACCGCAAACC-GAAGTCGGCGGCTTTTCTGCT, which is located between 1998 bp and 2047 bp, for detection of the amplified UidA gene; a 1350 bp region of the UidA gene is amplified using the aforementioned primers 745L-1 and 2065R-1 and using either aforementioned gene probe UidA-1 or UidA-2 for detection of the amplified UidA gene; and a 153 bp region of the UidC gene the controller region of the UidA gene and based on the sequence reported by Balnco et al., MGG, 199:101–105 (1985), is amplified using the primers 301L-1, 5'-TGTTACGTCCTGTAGAAAGCCC, and 432R-1, 5'-AAAACTGCCTGGCACAGCAATT, which are located between 301 bp and 322 bp and 432 bp and 453 bp, respectively, and using the gene probe UidC-1, 5'-CAACCCGTGAAATCAAAAAACT-CGACGGCCTGTGGGCATT, which is located between 323 bp and 362 bp, for detection of the amplified UidC gene.

Detection of Amplified Targeted Coliform DNA Sequences

PCR amplified targeted coliform DNA sequences were detected by using gel electrophoresis and radiolabelled gene probes. The amplified target DNA references were separated using either 0.8-1% horizontal agarose gels or 5% vertical polyacrylamide gels. Agarose gels were run in TAE buffer (0.04M Tris-acetate and 0.001M EDTA, pH 8.0). Polyacrylamide gels were run in TBE buffer (0.89M Tris-borate, 0.089M boric acid and 0.002M EDT, pH 8.0) at 5.7-9.0 V/cm for 2-4 h. The gels were stained in $2 \times 10^{-4}$% ethidium bromide solution, visualized with a Photo/PrepI UV transilluminator (Fotodyne Inc., New Berlin, Wis.) and photographed.

For Southern blots the amplified target DNA sequences were transferred onto nylon membranes (ICN Biomedicals, Costa Mesa, Calif. or BioRad, Richmond, Calif.) using 0.4M NaOH solution and fixed onto the membranes either by baking for 1 h at 80° C. or by UV irradiation. For dot blots, the double-stranded amplified target DNA sequences were denatured by adding a denaturing solution containing 0.1 volume 3M NaOH and 0.1M Na$_2$EDTA, incubated at 60° C. for 15 min-1 h, and neutralized with 1 volume cold 2M ammonium acetate; the samples were then spotted onto Zeta probe nylon membranes (BioRad, Richmond, Calif.) using a BioRad dot blot manifold at a 4-5 psi vacuum pressure.

The amplified DNAs immobilized on the ICN nylon membranes were prehybridized with a hybridization solution containing 5×SSPE (1×SSPE is 10 mM sodium phosphate, pH 7.0, 0.18 m NaCl, 1 mM Na$_2$EDTA), 0.5% SDS, 5% Denhardt's solution, and 100 µg per ml phenol extracted, denatured, salmon sperm DNA (Sigma) or 50 µg per ml type X Baker's yeast tRNA (Sigma); prehybridization was at 55°-60° C. for 3-16 h. The blots were washed twice in 2×SSPE, 0.5% SDS at room temperature for 10 min each and once in 0.1×SSPE, 0.1% SDS at 55° C. for 3-5 min with gently agitation. To detect 32P-labelled DNAs, the blots were covered with saran wrap (Fisher Biochemical, Pittsburgh, Pa.) and x-ray film (Kodak X-AR film, Eastman Kodak Co., Rochester, N.Y.) was placed over them; film exposure was at −70° C. for 1-48 h.

A 50 mer gene probe LZ-1, 5'-TGACGTCTCGTTGCTGCATAAACCGAC-TACACAAATCAGCGATTTCCATT, was used for detection of amplified lacZ and a 50 mer gene probe LB-1 5'-TGCGTGATAACTATCGTCTGGTT-GATGGCGCATCGAAAGACGGCTGGTTG, was used for detection of amplified lamB. Both gene probes hybridize to target sequences located within the respective regions of amplified target DNA sequences. The gene probes were 5'-end radiolabelled with [$^{32}$P]ATP (>3000 Ci/mmol) by a procedure in which a 30 µl reaction solution contained 50 mM Tris-HCl, pH 7.5, 10 mM MgCl$_2$, 5 mM DTT (Sigma Chemical, St. Louis, Mo.), 1 mM KCl, 1-10 µG oligonucleotide gene probe, 120 pmol [$^{32}$P]ATP (specific activity >3000 Ci/mmol) (New England Nuclear Corp., Boston, Mass.), 1 mM spermidine (disodium salt), and 20 units of T4 polynucleotide kinase (U.S. Biochemical). The reaction mixture was incubated at 37° C. for 1 h and the radiolabelled probes were purified by using a Sephadex G-50 column and TE buffer (10 mM Tris-Cl, pH 7.6, 1 mM Na$_2$EDTA).

Specificity of Coliform Detection

To illustrate the specificity of coliform detection by PCR amplification of regions of lacZ, lamB, UidA and UidC tests were conducted using the following bacterial strains: *Escherichia coli* ATCC 11775, *E. coli* ATCC 10798, *E. coli* ATCC 5224, *E. coli* ATCC 25404, *E. coli* (lamB−) ATCC 23556, *E. coli* (lamB−) ATCC 23737, *E. coli* (lamB−) ATCC 23739, *E. coli* (lamB−) ATCC 12435, *Enterobacter cloacae* ATCC 13047, *Salmonella typhimurium* ATCC 19585, *Citrobacter fuendii* ATCC 33128, *Klebsiella pneumonia* ATCC 13883, *Shigella flexineri* ATCC 12022, *Shigella sonnei* ATCC 25931, *Pseudomonas putida* mt-2, *Streptococcus lactis* ATCC 19435, and 32 environmental isolates from m-Endo enumeration plates and identified as *E. coli* by using Enterotubes (Roche). All enterobacteria, including *E. coli* strains, were grown in 2 x YT liquid broth (10 g Bacto-tryptone, 10 g Yeast extract, 5 g NaCl per liter), TYE agar (2 x YT+14 g/l Bacto agar) at 35° C.; *Pseudomonas putida* were grown on Pseudomonas isolation agar at 30° C.; *Streptococcus lactis* was grown on litmus milk agar (Difco) at 37° C. DNAs were extracted for 12-16 h from cultures of these bacteria and 50 ng-1µg of recovered DNAs subjected to PCR amplification as previously described using varying annealing temperatures during the PCR procedure; gene probes were used to detect amplified DNA sequences by both Southern and dot blot procedures as described hereinbefore. The specific activities of the radiolabelled probes were 68,000-167,000 DPM/µg DNA.

Sensitivity of Coliform Detection

To illustrate the sensitivity of PCR amplification-gene probe detection of *E. coli*, 1 µg of genomic DNA from *E. coli* (Sigma, St. Louis, Mo.) was serially diluted to establish a concentration range of 1 ag-1 µg. A control with 0 g *E. coli* DNA was also included. The samples were then subjected to PCR amplification using either primers BL4910 and BR5219 for lamB or primers ZL1675 and ZR2548 for lacZ; amplified DNA was analyzed by dot blot using gene probes LB-1 and LZ-1. One microgram of *P. putida* genomic DNA and 1 µg of Salmon sperm DNA were also subjected to PCR using the same primers and PCR conditions as negative controls and to determine the background signal of the hybridization reaction. One-tenth of each of the amplified samples (10 µl) was used for dot blot analysis.

Additionally, serial dilutions in 0.1M phosphate buffer (pH 7.2) of an overnight (16 h) culture of *E. coli* ATCC 11775 grown in 2×YT broth at 37° C. were used to determine the sensitivity of PCR amplification of lamB for coliform detection. Dilutions were performed using 100 ml autoclave sterilized tap water treated with 0.1% sodium thiosulfate for dechlorination. In addition to the *E. coli* cells from the serial dilutions, ca. 1×10$^9$ cells of *Pseudomonas putida* were added to each dilution blank to serve as a nontarget background population and to facilitate collection of bacterial cells from the samples. Bacterial cells were collected by centrifugation at 12,000×g for 10 min in a Sorvall RS-5 centrifuge; the pellets were resuspended in a small volume of sterile dechlorinated tap water, transferred to 1.5 ml microfuge tubes and resedimented by centrifugation at 12,000×g for 5 min. The cells were suspended in PCR buffer and PCR amplifications and gene probe detections were performed as described above for lamB.

To determine the number of viable *E. coli* cells in each dilution, replicate aliquots of the serial dilutions were plated onto m-Endo agar. CFUs of the target *E. coli* cells were determined by counting colonies with typical coliform appearance after 24 h incubation at 37° C. Direct counts were performed using the acridine orange direct count procedure.

TEST RESULTS

Specificity of Coliform Detection by PCR Amplification of lacZ

PCR amplification using primers ZL-1675 and ZL-2548 and a primer annealing temperature of 40° C. produced positive amplified DNA sequences for both coliform and noncoliform bacterial target DNA sequences. Using Citrobacter DNA as a template, the amplified DNA was larger than when *E. coli* DNA was the template, indicating a difference between the target lacZ genes between these organisms. The differences were also indicated by the differential response to increasing the primer annealing temperature between *E. coli* and other bacterial species tested. Raising the primer annealing temperature to 50° C. to increase the stringency of PCR eliminated amplification for all noncoliforms, e.g. *Pseudomonas putida* and *Streptococcus lactis*, but also eliminated amplification of some coliforms, e.g. *Enterobacter aerogenes* and Citrobacter. Using a primer annealing temperature of 50° C., lacZ amplification occurred with *Escherichia coli, Enterobacter cloacae* and to a lesser extent with *Klebsiella pneumoniae*. Southern blots showed hybridization with the LZ-1 gene probe indicating amplification of the target lacZ only with *E. coli*, *Ent. cloacae*, and *K. pneumoniae*, even when nonstringent primer annealing temperature of 40° C. was employed. Amplification and hybridization for lacZ also occurred for *E. coli* and *Ent. cloacae* using primer annealing temperature of 60° C. and 70° C. All strains of *E. coli* tested, including the 32 environmental isolates, showed positive DNA amplification and hybridization with the gene probe for lacZ at the predicted position for 875 bp. Shigella DNA also was amplified and detected.

Because amplification with primers ZL-1675 and ZL-2548 did not form the basis for "total coliform" detection equivalent to total coliform enumeration by viable count procedures, a shorter region of lacZ nearer the amino terminal and of the active site was amplified using primers ZL-1675 and ZR-2025 and a primer annealing temperature of 50° C. The region amplified using these primers was sufficiently conserved to provide a basis for PCR and gene probe detection of "total coliforms". There was some variation, however, between the various coliforms species tested with regard to the sizes of amplified DNAs, indicating some heterogeneity in the gene sequence. The use of lacZ amplification permitted detection of Shigella but not Salmonella so that some enteric pathogens would not be directly detected by this method. Like Salmonella, noncoliforms were not amplified or detected.

Specificity of Coliform Detection by PCR Amplification of lamB

PCR amplification of lamB, like that of lacZ, produced additional nonspecific DNA amplification, including amplification of noncoliform DNAs when primer annealing temperatures were below 50° C. Using primers BL-4899 and BR-5452 and primer annealing temperatures of 60° C., however, limited the range of bacteria showing positive DNA amplification; *E. coli*, including all lamB⁻ stains tested, *S. typhimurium* and Shigella spp. were the only bacteria that showed amplification of lamB when a primer annealing temperature of 60° C. was used as detected by hybridization with gene probe LB-1. Raising the primer annealing temperature still further, to 70° C., eliminated amplification of *S. typhimurium*, but still permitted amplification of *E. coli* and Shigella spp.

Using the second set of primers, BL-4910 and BR-5219, and a primer annealing temperature of 50° C., only *E. coli*, including all lamB⁻ stains tested, *S. typhimurium*, and Shigella spp. showed amplification of the target 309 bp region that hybridized with gene probe LB-1. *S. typhimurium* DNA failed to amplify with these primers when a primer annealing temperature of 60° C. was used, whereas *E. coli*, including the 32 environmental isolates, and Shigella spp. still showed amplification of target DNAs. Thus, using these primers for lamB and a primer annealing temperature of 60° C. during PCR amplification permitted detection of *E. coli* and Shigella; using the lower primer annealing temperature of 50° C. permitted detection of these enteric bacteria and also Salmonella. These results indicate that the primer annealing temperature should be close to the Tm to minimize nonspecific amplification. They also suggest that besides *E. coli*, Salmonella and Shigella may have at least a portion of the lamB gene. Hence, PCR amplification of lamB, as demonstrated here, provides a means of monitoring the indicator bacterial species of fecal contamination, *E. coli*, and also of the principal enteric bacterial pathogens that cause water-borne disease outbreaks, Salmonella and Shigella. Therefore, the bacteria associated with human fecal contamination of waters, both indicator and pathogens, is detectable by PCR amplification and gene probes for lamB.

Specificity of Coliform Detection by PCR Amplification of UidA and UidC

Amplification using UidA and UidC primers was achieved using a primer annealing temperature of 50° C.

Amplification with the primer pair UidA.745L-1 and UidA.879R-1 formed a 147 bp product. This product was detected using radiolabelled gene probe UidA-1. When the same strains were tested as for lamB and lacZ, only *Escherichia coli* (all strains tested) *Shigella sonnei*, and *Shigella flexineri* gave positive signals as detected by dot blot and Southern blot analysis.

Amplification with the primer pair UidA.1939L-1 and UidA.2085R-1 formed a 166 bp product. This product was detected using radiolabelled gene probe UidA-2. When the same strains were tested as for lamB and lacZ, only *Escherichia coli* (all strains tested), *Shigella sonnei*, and *Shigella flexineri* gave positive signals as detected by dot blot and Southern blot analysis.

Amplification with the primer pair UidA.745L-1 and UidA.2085R-1 formed a 1350 bp product. This product was detected using radiolabelled gene probe UidA-2. When the same strains were tested as for lamB and lacZ, only *Escherichia coli* (all strains tested) and *Shigella sonnei* gave positive signals as detected by dot blot and Southern blot analysis.

Amplification with the primer pair UidC.301L-1 and UidC.432R-1 formed a 153 bp product. This product was detected using radiolabelled gene probe UidC-1. When the same strains were tested as for lamB and lacZ, only *Escherichia coli* strains tested) and *Shigella sonnei* gave positive signals as detected by dot blot and Southern blot analysis.

Sensitivity of Coliform Detection by PCR Amplification of lacZ and lamB

Besides appropriate selectivity for target coliforms, to be useful for monitoring purposes, a PCR-gene probe approach must provide sufficient sensitivity to ensure the safety of potable water supplied. A target sensitivity of 1 cell per 100 ml, which is as good as viable culture methods is desirable. The sensitivity of detection was found to depend upon the PCR conditions. Raising the primer annealing temperature, which as already discussed enhanced the selectivity of DNA amplification to target cells, lowered the sensitivity of detection. Thus, using a primer annealing temperature of 70° C. permitted amplification and detection of lacZ when more than 100 fg of genomic *E. coli* DNA, ca. 1 ag of target DNA, was present but not with lower amounts of DNA. In contrast as low as 1–10 fg of *E. coli* DNA could be detected by PCR amplification of lacZ when a primer annealing temperature of 40° C. was used; the same detection limit was found using lamB amplification. The detection of 10 fg of genomic DNA was reliable. At 1 fg genomic DNA approximately 22% of the samples gave positive signals which closely corresponds to the expected Poisson distribution of the target gene at that concentration of genomic DNA. Concentrations of *E. coli* DNA below 1 fg did not show positive amplification and detection by hybridization with gene probes. The sensitivity of detection achieved by amplification of lacZ and lamB coupled with 32P-labelled gene probes is equivalent to 1–10 ag of target DNA, i.e. single genome copy, single cell, detection.

The direct lysis procedure using cells recovered by centrifugation also indicated sensitive detection of *E. coli* by PCR amplification and gene probe analysis. As few as 1–5 viable cells per 100 ml water sample were detected. Similarly, as few as 1 viable cell in a sample was detected using amplification of lamB.

The use of PCR and gene probes has been demonstrated to provide both the specificity and sensitivity necessary as a basis for a method for monitoring coliforms as indicators of human fecal contamination of waters. The PCR amplification of lacZ using primers ZL-1675 and ZR-2025 and an annealing temperature of 50° C. permits the detection of most coliforms and the PCR amplification of lamB using primers BL-4910 and BR-5219 and an annealing temperature of 60° C. enables the specific detection of low levels of the enteric indicator organism, i.e. *E. coli* and the enteropathogenic pathogens of concern, i.e. Salmonella and Shigella. The PCR amplification of lacZ also permits a rapid and reliable means of assessing the bacteriological safety of waters and provides an effective alternative methodology to the conventional viable culture methods. PCR amplification of targeted DNA also permits the sufficient sensitivity and specificity for direct detection of pathogens in environmental samples, rather than relying upon the indirect detection of indicator organisms.

LEGIONELLA SPECIES

Growth of Legionella and Recovery of Legionella DNA

Bacterial strains used in this study are listed hereinafter in Table 1. Additionally, seven fresh environmental isolates of *Legionella pneumophila* were included. These environmental strains were isolated from cooling towers and identified based upon phenotypic characteristics, including lack of growth on media lacking cysteine, and serological reactions, including positive reactivity with a monoclonal antibody reagent (Genetic Systems, Seattle) specific for *L. pneumophila.*

TABLE 1

| | BACTERIAL STRAIN | | |
|---|---|---|---|
| Genus Species Subspecies | Strain | Serogroup | Source |
| 1. *Legionella pneumophila* | (Knoxville-1) | 1 | CDC |
| 2. *L. pneumophila* | (Togus-1) | 2 | CDC |
| 3. *L. pneumophila* | (Bloomington-2) | 3 | CDC |
| 4. *L. pneumophila* | (Los Angeles-1) | 4 | CDC |
| 5. *L. pneumophila* fraseri | (Los Angeles-1) | 4 | ATCC 33156 |
| 6. *L. pneumophila* | (Dallas-1E) | 5 | CDC |
| 7. *L. pneumophila* fraseri | (Dallas-1E) | 5 | ATCC 33823 |
| 8. *L. pneumophila* | (Chicago-2) | 6 | CDC |
| 9. *L. pneumophila* | (Chicago-8) | 7 | ATCC 33823 |
| 10. *L. pneumophila* pneumophila | (Concord-3) | 8 | ATCC 35096 |
| 11. *L. pneumophila* pneumophila | (IN-23-G1-CS) | 9 | ATCC 35289 |
| 12. *L. pneumophila* pneumophila | (Leiden) | 10 | ATCC 43283 |
| 13. *L. pneumophila* pneumophila | (797-PA-H) | 11 | ATCC 43130 |
| 14. *L. pneumophila* pneumophila | (570-PA-H | 12 | ATCC 43290 |
| 15. *L. pneumophila* pneumophila | (82A3105) | 13 | ATCC 43736 |
| 16. *L. pneumophila* pneumophila | (1169-MN-H) | 14 | ATCC 43703 |
| 17. *L. pneumophila* fraseri | | Lansing 3 | ATCC 35251 |
| 18. *L. pneumophila* pascullei | (V8W) | 5 | ATCC 33737 |
| 19. *L. bozmanii* | | | CDC |
| 20. *L. erythra* | SF33P | | U of L |
| 21. *L. feelei* | | | CDC |
| 22. *L. longbeachae* | | 1 | CDC |
| 23. *L. longbeachae* | Tucker 1 | 2 | ATCC 33484 |
| 24. *L. jordanis* | | | CDC |
| 25. *L. dumoffii* | | | CDC |
| 26. *L. micdadei* | | | CDC |
| 27. *L. gormanii* | | | CDC |
| 28. *Pseudomonas aeruginosa* | | | ATCC 27853 |
| 29. *P. fluorescens* CDC 93 | | | CDC |
| 30. *P. fluorescens* EB | | | CDC |
| 31. *P. maltophilia* | | | CDC |
| 32. *P. alcaligenes* ABB 50 | | | CDC |
| 33. *Flavobacterium* CDC 65 | | | CDC |
| 34. *Salmonella typhimurium* | | | ATCC 19585 |
| 35. *Shigella flexineri* | | | ATCC 12022 |
| 36. *Escherichia coli* | | | ATCC 12435 |

All Legionella, Pseudomonas, and Flavobacterium strains were grown in a liquid medium consisting of 10 g yeast extract (Difco, Detroit) and 10 g ACES (N-[2-acetamido]-2-aminoethane-sulfonic acid) per liter, adjusted to pH 7.0 with KOH, and supplemented after autoclaving with 0.25 g each of L-cysteine and soluble ferric pyrophosphate (Sigma, St. Lous). Enterobacteria were grown in 2×YT liquid broth (10 g Bacto-tryptone, 10 g Yeast extract, 5 g NaCl per liter), and TYE agar (2×YT+14 g/l Bacto agar) at 35° C.[26]. After overnight growth at 37° C. with constant shaking at 120 rpm, chromosomal DNA was isolated. DNA was released from bacterial cells in 1.5 ml samples of overnight cultures by alkaline lysis with SDS treatment. Proteinase K and CTAB:NaCl were used to remove proteins and carbohydrates and the DNA was further purified by using chloroform:isoamyl alcohol (24:1) followed by phenol:chloroform:isoamyl alcohol (24:24:2) extractions. DNA was then precipitated by isopropanol and pelleted by centrifugation at 12,000×g for 15 min. The DNA pellets were washed once with cold 70% alcohol and dried under vacuum. Similarly, total genomic DNAs from all environmental isolates were isolated following the DNA extraction procedure as described above. Using this procedure 1001-150 μg of purified genomic DNA were recovered from each bacterial culture.

PCR Amplification of Targeted Leoionella Sequences

PCR amplification was performed using a DNA Thermal Cycler with Amplitag DNA polymerase (Perkin Elmer Cetus Corp.). The PCR solution contained 1×PCR amplification buffer (10×buffer contains 50 mM KCl, 100 mM Tris-Cl, pH 8.13, 15 mM MgCl$_2$ and 0.1% (w/v) gelatin), 200 μM each of the dNTPs, 0.5 μM of each of the primers, 1 fg-1 μg template DNA, 2.5 units Amplitag, and double distilled water containing 0.1% diethylpyrocarbonate (DEPC). In some tests the concentration of total magnesium ions in the PCR reactions was varied over the range of 0.8 mM-4 mM total Mg$^{++}$; other components in the PCR mixture were maintained at the concentration of the manufacturer's standard 10×PCR reaction buffer. Template DNAs were initially denatured at 94° C. for 1-3 min. Then a total of 25-30 PCR cycles were run. In the PCR cycles DNAs were denatured at 94° C. for 1 min and primers were annealed and extended at 50° C. for 1 min. In some tests, primer annealing temperatures of 60° C. and 70° C. also were used. Oligonucleotide primers were synthesized using an applied Biosystems Model DNA synthesizer and purified using an oligonucleotide Purification Cartridge (Applied Biosystems, Foster City, Calif.) for small samples and reverse-phase HPLC with a C-8 3 micron reverse-phase column (Perkin Elmer) for large samples.

A 104 bp region of the Legionella 5S rRNA coding gene, based upon the sequence reported by MacDonell and Colwell, Nucleic Acids Research, 1335 (1987), was amplified by using 20 mer primers L5SL9 (5'-ACTATAGCGATTTGGAACCA-3') and L5SR93 (5'-GCGATGACCTACTTTCGCAT-3'). Primer L5SL9 was located between 9 bp and 28 bp and primer L5SR93 was located between 93 bp and 112 bp of the 5S rRNA gene. A 650 bp sequence of the coding region of the L. pneumophila macrophage infectivity potentiator (mip) gene, based upon the sequence reported by Engleberg et al., Israel J. Med. Sci. 22:703-705 (1986), was amplified by using two 21 mer primers. Primer LmipL920 (5'-GCTACAGACAAGGATAAGTTG-3') was located between 920 bp and 940 bp and primer LmipR1548 (5'-GTTTTGTATGACTTTAATTCA-3') was located between 1548 bp and 1569 bp of the mip gene.

Detection of Amplified Targeted DNAs Legionella Sequences

PCR amplified Legionella DNA sequences were detected by using gel electrophoresis and radiolabelled gene probes. The amplified targeted DNA sequences were separated using either 0.8-1% horizontal agarose gels or 5% vertical polyacrylamide gels. Agarose gels were run in TAE buffer (0.04M Tris-acetate and 0.001M EDTA, pH 8.0). Polyacrylamide gels were run in TBE buffer (0.089M Tris-borate, 0.089M boric acid and 0.002M EDTA, pH 8.0) at 5.7-9.0 V/cm for 2-4 h. The gels were stained in 2×10$^{-4}$% ethidium bromide solution, and visualized with a Photo/PrepI UV transilluminator (Fotodyne Inc., New Berlin, Wis.).

For Southern blots the DNAs were transferred onto nylon membranes (ICN Biomedicals, Costa Mesa, Calif. or BioRad, Richmond, Calif.) using 0.4M NaOH denaturing solution and fixated onto the membranes either by baking for 1 h at 80° C. or by UV irradiation. For dot blots, the double-stranded amplified DNAs were denatured by adding a denaturing solution containing 0.1 volume 3M NaOH and 0.1M disodium EDTA, incubated at 60° C. for 15 min, and neutralized with 1 volume cold 2M ammonium acetate; the samples were then spotted onto Zeta probe nylon membranes (BioRad, Richmond, Calif.) using a Schleicher and Scheuell slot blot manifold at a 4-5 psi vacuum pressure.

The amplified DNAs immobilized on the ICN nylon membranes were prehybridized with a solution containing 5×SSPE (1×SSPE is 10 mM sodium phosphate, pH 7.0, 0.18M NaCl, 1 mM EDTA), 0.5% SDS, 5% Denhardt's solution, and 100 μg/ml phenol extracted, denatured, salmon sperm DAN (Sigma), or 50 μg/ml type X Baker's yeast tRNA (Sigma). For DNAs immobilized on Zeta probe membranes, 0.5M NaH$_2$PO$_4$ (pH 7.2), 1 mM Na$_2$EDTA, and 7% SDS solution was used for prehybridization. Prehybridization with both types of membranes was at 55°-60° C. for 15-20 min. After removal of the prehybridization buffer, the membranes were hybridized with fresh hybridization solution containing 200-300 ng of denatured radiolabelled gene probe and incubated at 55°-60° C. for 3-16 h with gentle shaking. The blots were washed twice in 2 x SSPE, 0.5% SDS at room temperature for 10 min and once in 0.1 x SSPE, 0.1% SDS at 55°-60° C. for 3-5 min with gentle agitation. To detect 32P-labelled DNAs, the blots were covered with saran wrap (Fisher Biochemical, Pittsburgh, Pa.) and x-ray film (Kodak X-AR film, Eastman Kodak Co., Rochester, N.Y.) was places over them. All films were exposed at −70° C. for 1-48 h.

The gene probes were 5'-end radiolabelled with [P$^{32}$]ATP (>3000 Ci/mmol) (New England Nuclear Corp., Boston, Mass.) by a procedure in which the 30 μl reaction solution used in this procedure contained 50 mM Tris-Cl, pH 7.5, 10 mM MgCl$_2$, 5 Mm DTT (Sigma Chemical, St. Louis, Mo.), 1 mM KCl, 10 μg oligonucleotide gene probe (120 pmol [P$^{32}$P]ATP (specific activity >3000 Ci/mmol), 1 mM spermidine (disodium salt), and 20 units of T4 polynucleotide kinase (U.S. Biochemical) The reaction mixture was incubated at 37° C. for 1 h and the radiolabelled probes were purified by using a Sephadex G-50 column and TE buffer [10 mM Tris-Cl, pH 7.6, 1 mM EDTA (disodium salt)]or by using a Centricon 10 column (Amicon Corp., Danvers, Mass.).

A 50 mer gene probe L5S-1, 5'-CTCGAACTCAGAAGTCAAACATTTCCGCGCCAATGATAGTGTGAGGCTTC, was used for detection of the amplified 5S RNA coding gene.

A 50 mer gene probe Lmip-1, 5'-TTTGGGGAAGAATTTTAAAAATCAAGGCATAGATGTTAATCCGGAAGCAA, was used for detection of amplified mip gene.

Specificity of Legionella and L. pneumophila Detection

To illustrate the specificity of total Legionella detection by PCR amplification-gene probe methods, 50 ng of DNA from each of the strains listed in Table 1 was tested alone and in combination with 50 ng of DNA from known Legionella species to further examine the specificity of amplification and detection and also to determine whether non-target DNAs would interfere with this method of Leoionella detection.

Similarly, for specific detection of

L. pneumophila, 50 ng of DNA from each of these bacterial strains was subjected to PCR amplification using LmipL920 and LmipR1548 primers. Additionally, a 50 ng mixture of DNAs from all the non-*L. pneumophila* species of Legionella listed in Table 1 was tested alone and in combination with 50 ng mixture of DNA from known strains of *L. pneumophila* to further examine the specificity of amplification and detection and also to determine whether non-target DNAs would interfere with this method of *L. pneumophila* detection.

Agarose gel electrophoresis was used to observe DNA amplification. Radiolabelled gene probes and Southern blot analysis were used to confirm amplification of the target gene sequences.

Sensitivty of Legionella Detection

To illustrate the sensitivity of PCR amplification-gene probe detection of *L. pneumophila,* 1 μg of genomic DNA from *L. pneumophila* was serially diluted to establish a concentration range of 1 ag ($10^{-18}$ g)−1 μg genomic DNA (ca. $10^{-4}$ ag−$10^{2}$ pg target DNA). A negative control without Legionella DNA was also included. The samples were then subjected to PCR amplification using primers LmipL920 and LmipR1548, and analyzed by the slot blot method using gene probe Lmip-1. One microgram *E. coli* genomic DNA and 1 μg salmon sperm DNA were also subjected to PCR amplification using the same primers and PCR conditions as negative controls and to determine the background signal of the hybridization reaction. One-tenth of each of the amplified samples (10 μl) was used for slot blot analysis.

TEST RESULTS

Specificity of Legionella Detection by PCR Amplification of 5S rRNA

PCR amplification using primers L5SL9 and 5SR93 and a primer annealing temperature of 50° C. produced positive amplified DNA bands for all Legionella species tested, including the seven environmental isolates of *L. pneumophila.* Faint bands were also observed for *P. fluorescens* EB, *P. fluorescens* CDC 93 and *P. maltophilia.* The same pattern was also seen when the primer annealing temperature was increased to 60° C. to eliminate nonspecific amplification. These Pseudomonas strains cross-react with Legionella-directed antibody when stained with direct fluorescence antibody (DFA), suggesting that they are related in some ways to Legionella. Southern blots with the L5S-1 probe, however, showed hybridization only with Legionella amplified DNA, demonstrating specific detection of the amplified target 5S rRNA sequence. No bands were observed and no hybridization occurred with any of the other non-Legionella amplified samples, indicating that the primers L5SL9 and L5SR93 together with gene probe L5S-1 provides the basis for specific detection system for Legionella species.

Moreover, no DNA amplification was found using the mixture of DNAs from the non-Legionella species unless Legionella DNA was also added, indicating that amplification of the 5S rRNA coding segment was specific for Legionella species and that non-target DNA does not interfere with detection of the target gene segment.

All the Legionella strains showed amplification of the target gene sequence at final concentrations of 1.5 mM–4 mM of $MgCl_2$ in the PCR reactions. Typically, optimum amplification occurred at 1.5 mM of $MgCl_2$ (final concentrations).

Specificity of *L. pneumophila* Detection by PCR Amplification of mip

PCR amplification using primers LmipL920 and LmipR1548 and a primer annealing temperature of 50° C. produced positive amplified DNA bands for all *L. pneumophila* strains tested. No non-*L. pneumophila* species, neither the other Legionella species nor any of the other genera tested, showed DNA amplification using the primers for mip. Southern blot hybridizations with the mip-1 gene probe indicated amplification of the target mip sequence was specific for *L. pneumophila.* Additionally, no DNA amplification of the mip gene was detected using the mixture of DNA from the non-*L. pneumophila* strains unless DNA from *L. pneumophila* was added to the mixture.

Two strains, *L. pneumophila* Knoxville-1 (serogroup 1) and *L. pneumophila* Los Angeles-1 (serogroup 4) showed amplification at lower final concentrations of $MgCl_2$—1.0 mM and 1.0 mM, respectively, than the other Legionella species. These same two strains had optimal magnesium concentrations for PCR amplification of 3.5 and 2.5 mM $MgCl_2$, respectively, which were higher than the optimal 1.5 mM $MgCl_2$ for the other strains of *L. pneumophila.*

Sensitivity of Legionella Detection by PCR Amplification

Using primers for the amplification of the mip gene, detected consistently by hybridization with mip-1 probe. This is equivalent to approximately 0.1 ag of target DNA which represents the detection of a single *L. pneumophila* mip gene segment. When 1 fg of the genomic DNA from *L. bozmanii* and *L. pneumophila* was amplified using L5SL9 and L5SR93 primers, approximately 18% of the samples were detected with the probe for the 5S rRNA in Legionella. This pattern of positive amplification results corresponds to the expected Poisson distribution of the target gene at that concentration of the genomic DNA.

The specificity of amplification of the target DNA sequences using the process of this invention permits the detection of all Legionella in a sample based upon the 5S rRNA coding DNA segment and specifically the detection of *L. pneumophila* based upon the mip gene. The specificity demonstrated indicates that this process provides a method for both clinical diagnosis and environmental monitoring of Legionella and *L. pneumophila.* The level of Legionella detection using the PCR-gene probe method was consistent with detection of single cells of *L. pneumophila.* The ability to specifically detect such low numbers of Legionella establishes a methodological basis for both clinical diagnosis of individuals with legionellosis and environmental monitoring of water and clinical samples to ensure the safety of hospitals, portable water supplies, cooling towers and possible other sources of Legionella and to identify the sources of *L. pneumophila* when outbreaks of Legionnaire's disease occur. Using multiple primers one can detect both all Legionella species and all *L. pneumophila* serotypes in the same sample at the same time.

It will be apparent to those skilled in the art that the foregoing description is merely illustrative of the invention and that the invention has numerous embodiments not specifically exemplified.

We claim:

1. A process for detecting the presence of water-borne pathogens and indicator microorganisms of bacteria primarily of fecal origin in an environmental water sample, said process comprising:
   (1) recovering from a water sample and concentrating into a suitably sized concentrated test sample of target cells substantially all water-borne pathogens and indicator microorganisms in said water sample;
   (2) treating the concentrated test sample to lyse the target cells and recover substantially undegraded target cells DNAs;
   (3) selecting a target gene carried in said target cells and selecting a target DNA nucleotide sequence in said target gene and incubating said target DNA nucleotide sequence under amplification conditions with two selected oligonucleotide primers and DNA polymerase such that each primer sequence is complementary to and hybridizes to one of two separated strands of the target DNA nucleotide sequence and the polymerase extends the primers to make fully double-stranded replicas of the target DNA nucleotide sequence, and
   (4) detecting amplified target DNA to determine the presence or absence in the test sample of said water-borne pathogens or indicator microorganisms carrying the selected target DNA nucleotide sequence;
   wherein the target genes and bacteria are selected from the groups consisting of:
   the lacZ gene to detect all species from the genera Escherichia, Enterobacter, Citrobacter and Klebsiella;
   the lamB gene to detect *Escherichia coli* and all species from the genera Salmonella and Shigella in combination and,
   the Uida gene to detect *Escherichia coli, Shigella sonnei* and *Shigella flexineri* in combination.

2. A process according to claim 1 to amplify a target DNA nucleotide sequence coded by the lacZ gene to exclusively detect Escherichia, Enterobacter, Citrobacter and Klebsiella species.

3. A process according to claim 1 to amplify a target DNA nucleotide sequence coded by the lamB gene to exclusively detect *Escherichia coli* and *Salmonella typhinurium* and Shigella species.

4. A process according to claim 1 to amplify a target DNA nucleotide sequence coded by the UidA gene to exclusively detect *Escherichia coli, Shigella sonnei* and *Shigella flexineri.*

5. A process according to claim 2 wherein the primer sequences consist of all or a substantial part of 5'-ATGAAAGCTGGCTACAGGAAGGCC and 5'-CACCATGCCGTGGGTTTCAATATT, and the amplified target DNA has a size of approximately 876 bp.

6. A process according to claim 2 wherein the primer sequences consist of all or a substantial part of 5'-GGTTTATGCAGCAACGAGACGTCA and 5'-ATGAAAGCTGGCTACAGGAAGGCC, and and the amplified target DNA has a size of approximately 326 bp.

7. A process according to claim 2 wherein the amplified target DNA is detected by hybridization to a probe consist of all or a substantial part of 5'-TGACGTCTCGTTGCTGCATAAACCGAC-TACACAAATCAGCGATTTCCATT or a complement of this sequence.

8. A process according to claim 3 wherein the primer sequences consist of all or a substantial part of 5'-GGATATTTCTGGTCCTGGTGCCGG and 5'-ACTTGGTGCCGTTGTCGTTATCCC, and the amplified target DNA has a size of approximately 554 bp.

9. A process according to claim 3 wherein the primer sequences consist of all or a substantial part of 5'-CTGATCGAATGGCTGCCAGGCTCC and 5'-CAACCAGACGATAGTTATCACGCA, and the amplified target DNA has a size of approximately 309 bp.

10. A process according to claim 3 wherein the amplified target DNA is detected by hybridization in a probe consisting of all or a substantial part of 5'-TGCGTGATAACTATCGTCTGGTTGATGGC-GCATCGAAAGACGGCTGGTTG or a complement of this sequence.

11. A process according to claim 4 wherein the primer sequences comprise all or a substantial part of 5'-AAAACGGCAAGAAAAAGCAG and 5'-ACGCGTGGTTACAGTCTTGCG and the amplified target DNA has a size of approximately 147 bp.

12. A process according to claim 4 wherein the primer sequences comprise all or a substantial part of 5'-TATGGAATTTCGCCGATTTT and 5'-TGTTTGCCTCCCTGCTGCGG and the amplified target DNA has a size of approximately 166 bp.

13. A process according to claim 4 wherein the primer sequences consisting of all or a substantial part of 5'-AAAACGGCAAGAAAAAGCAG and 5'-TGTTTGCCTCCCTGCTGCGG and the amplified target DNA has a size of approximately 1350 bp.

14. A process according to claim 4 wherein the amplified target DNA is detected by hybridization to a probe comprising 5'-TGCCGGGATCCATCGCAGGC-GTAATGCTCTACACCACGC-CGAACACCTGGG or 5'-AAAGGGATCTT-CACTCGCGACCGCAAACC-GAAGTCGGCGGCTTTTCTGCT or a complement of one of these sequences.

15. A kit for use in a process for detecting Escherichia, Enterobacter, Citrobacter and Klebsiella species in an environmental water sample, said method comprising a primary pair for amplification of a sequence in lacZ gene and a probe sequence for detection of an amplified sequence in the lacZ gene.

16. A kit for use in a process for detecting *Escherichia coli*, Salmonella species and Shigella species in an environmental water sample, said method comprising primer pairs for amplification of a sequence in the lamB gene and a probe sequence for detection of an amplified sequence in the lamB gene.

17. A kit for use in a process for detecting *Escherichia coli, Shigella sonnei,* and *Shigella flexineri* in an environmental water sample, said method comprising primer pairs for amplification of a sequence in the UidA gene and a detection probe sequence for detection of an amplified sequence in the UidA gene.

18. A kit according to claim 16 wherein the primer sequences comprise all or a substantial part of 5'-ATGAAAGCTGGCTACAGAAGGCC and 5'-CACCATGCCGTGGGTTTCAATATT, and the amplified target DNA has a size of approximately 876 bp.

19. A kit according to claim 15 wherein the primer sequences comprise all or a substantial part of 5'-

GGTTTATGCAGCAACGAGACGTCA and 5'-ATGAAAGCTGGCTACAGGAAGGCC, and and the amplified target DNA has a size of approximately 326 bp.

20. A kit according to claim 15 wherein the amplified target DNA is detected by hybridization to a probe consisting of all or a substantial part of 5'-TGACGTCTCGTTGCTGCATAAACCGAC-TACACAAATCAGCGATTTCCATT or a complement of this sequence.

21. A kit according to claim 16 wherein the primer sequences comprise all or a substantial part of 5'-GGATATTTCTGGTCCTGGTGCCGG and 5'-ACTTGGTGCCGTTGTCGTTATCCC, and the amplified target DNA has a size of approximately 554 bp.

22. A kit according to claim 16 wherein the primer sequences consisting of all or a substantial part of 5'-CTGATCGAATGGCTGCCAGGCTCC and 5'-CAACCAGACGATAGTTATCACGCA, and the amplified target DNA has a size of approximately 309 bp.

23. A kit according to claim 16 wherein the amplified target DNA is detected by hybridization in a probe consisting of all or a substantial part of 5'-TGCGTGATAACTATCGTCTGGTTGATGGC-GCATCGAAAGACGGCTGGTTG or a complement of this sequence.

24. A kit according to claim 17 wherein the primer sequences comprise all or a substantial part of 5'-AAAACGGCAAGAAAAAGCAG and 5'-ACGCGTGGTTACAGTCTTGCG and the amplified target DNA has a size of approximately 147 bp.

25. A kit according to claim 17 wherein the primer sequences comprise all or a substantial part of 5'-TATGGAATTTCGCCGATTTT and 5'-TGTTTGCCTCCCTGCTGCGG and the amplified target DNA has a size of approximately 166 bp.

26. A kit according to claim 17 wherein the primer sequences comprise all or a substantial part of 5'-AAAACGGCAAGAAAAAGCAG and 5'-TGTTTGCCTCCCTGCTGCGG and the amplified target DNA has a size of approximately 1350 bp.

27. A kit according to claim 17 wherein the amplified target DNA is detected by hybridization to a probe consisting of 5'-TGCCGGGATCCATCGCAGGC-GTAATGCTCTACACCACGC-CGAACACCTGGG or 5'-AAAGGGATCTT-CACTCGCGACCFFCAAACC-GAAGTCGGCGGCTTTCTGCT or a complement of one of these sequences.

* * * * *